(12) United States Patent
Young et al.

(10) Patent No.: US 8,414,617 B2
(45) Date of Patent: Apr. 9, 2013

(54) MULTI AXIAL CROSS LINK CONNECTOR SYSTEM FOR SPINAL IMPLANTS

(75) Inventors: J Stewart Young, Memphis, TN (US); Chris Johnson, Germantown, TN (US); Thomas Carls, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/187,191

(22) Filed: Jul. 20, 2011

(65) Prior Publication Data

US 2011/0282388 A1    Nov. 17, 2011

Related U.S. Application Data

(63) Continuation of application No. 10/695,067, filed on Oct. 28, 2003, now Pat. No. 8,029,543.

(51) Int. Cl.
*A61B 17/70* (2006.01)

(52) U.S. Cl. ........................................... 606/252

(58) Field of Classification Search ................. 606/246, 606/250–279; 403/391, 396, 399
See application file for complete search history.

(56) References Cited

U.S. PATENT DOCUMENTS

| | | | |
|---|---|---|---|
| 4,085,744 A | 4/1978 | Lewis et al. | |
| 4,404,967 A | 9/1983 | Bacal et al. | |
| 4,611,582 A | 9/1986 | Duff | |
| 5,005,562 A | 4/1991 | Cotrel | |
| 5,024,213 A | 6/1991 | Asher et al. | |
| 5,047,029 A * | 9/1991 | Aebi et al. | 606/264 |
| 5,108,395 A | 4/1992 | Laurain | |
| 5,147,360 A | 9/1992 | Dubousset | |
| 5,154,718 A | 10/1992 | Cozad et al. | |
| 5,261,907 A | 11/1993 | Vignaud et al. | |
| 5,368,594 A | 11/1994 | Martin et al. | |
| 5,439,463 A | 8/1995 | Lin | |
| 5,443,465 A | 8/1995 | Pennig | |
| 5,501,684 A * | 3/1996 | Schlapfer et al. | 606/301 |
| 5,549,607 A | 8/1996 | Olson et al. | |
| 5,651,789 A | 7/1997 | Cotrel | |
| 5,667,507 A | 9/1997 | Corin et al. | |
| 5,702,393 A | 12/1997 | Pfaifer | |
| 5,707,372 A | 1/1998 | Errico et al. | |
| 5,709,684 A | 1/1998 | Errico et al. | |
| 5,716,355 A | 2/1998 | Jackson et al. | |
| 5,752,955 A | 5/1998 | Errico | |
| 5,885,284 A | 3/1999 | Errico et al. | |
| 5,947,966 A | 9/1999 | Drewry et al. | |
| 5,980,523 A | 11/1999 | Jackson | |
| 6,077,263 A | 6/2000 | Ameil et al. | |

(Continued)

FOREIGN PATENT DOCUMENTS

WO    WO 96/39090    12/1996
WO    WO 02/30307 A2    4/2002

*Primary Examiner* — Eduardo C Robert
*Assistant Examiner* — Steven Cotroneo

(57) ABSTRACT

This invention relates to interconnection assemblies for use with spinal fixation systems to treat spinal defects. The interconnection assemblies can include various spinal rod connecting members and interconnecting elements to secure the spinal rod connecting members to each other in variable orientations and lengths. The interconnection assemblies can be adjusted to minimize interference with the spinal column, bony processes, and associated neural, muscular, and ligament components of the spine all the while exhibiting a low profile. The interconnecting elements and related components can be provided as a completely assembled unit that does not inadvertently become disassembled prior to or during implantation.

10 Claims, 15 Drawing Sheets

U.S. PATENT DOCUMENTS

| | | |
|---|---|---|
| 6,113,600 A | 9/2000 | Drummond et al. |
| 6,136,003 A | 10/2000 | Van Hoeck et al. |
| 6,217,578 B1 * | 4/2001 | Crozet et al. .................. 606/252 |
| 6,267,543 B1 * | 7/2001 | David et al. ................... 411/552 |
| 2001/0047171 A1 | 11/2001 | Troxell et al. |
| 2004/0116928 A1 | 6/2004 | Young et al. |

* cited by examiner

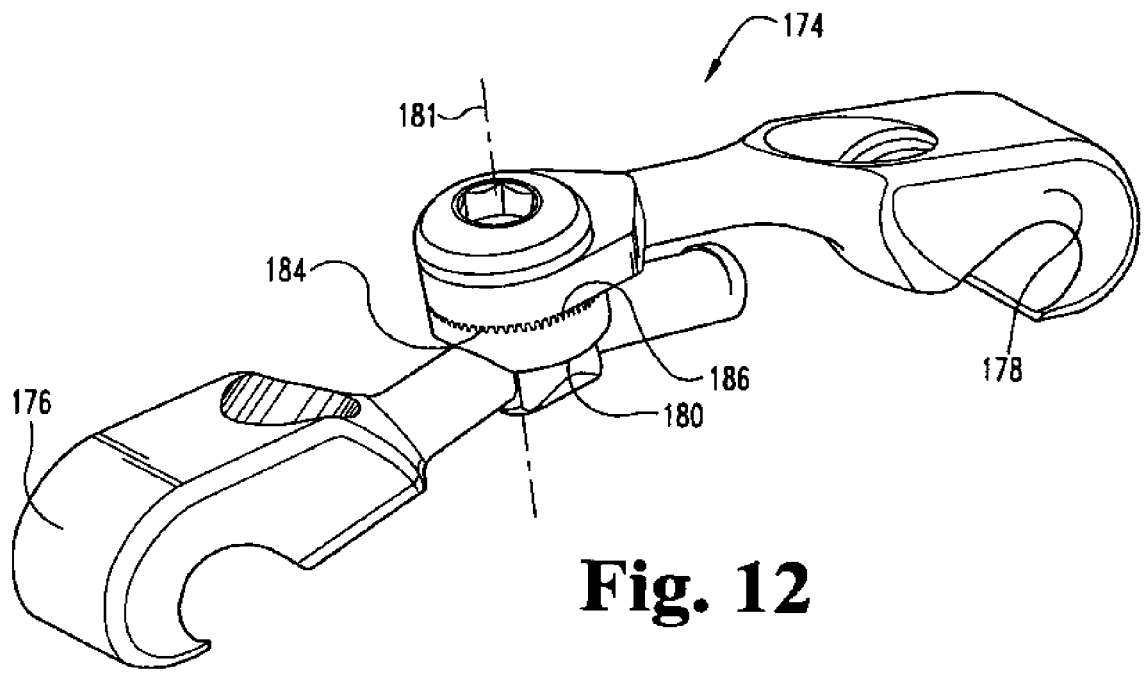
Fig. 12
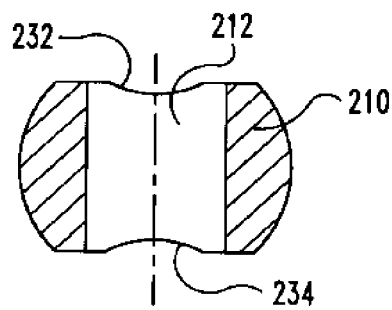
Fig. 14a
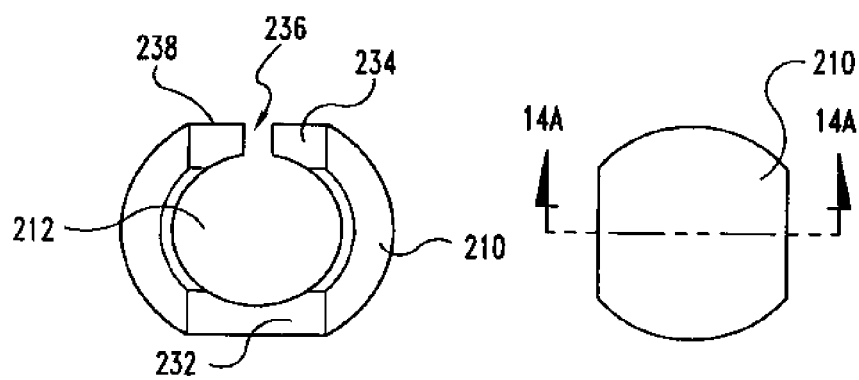
Fig. 14b  Fig. 14

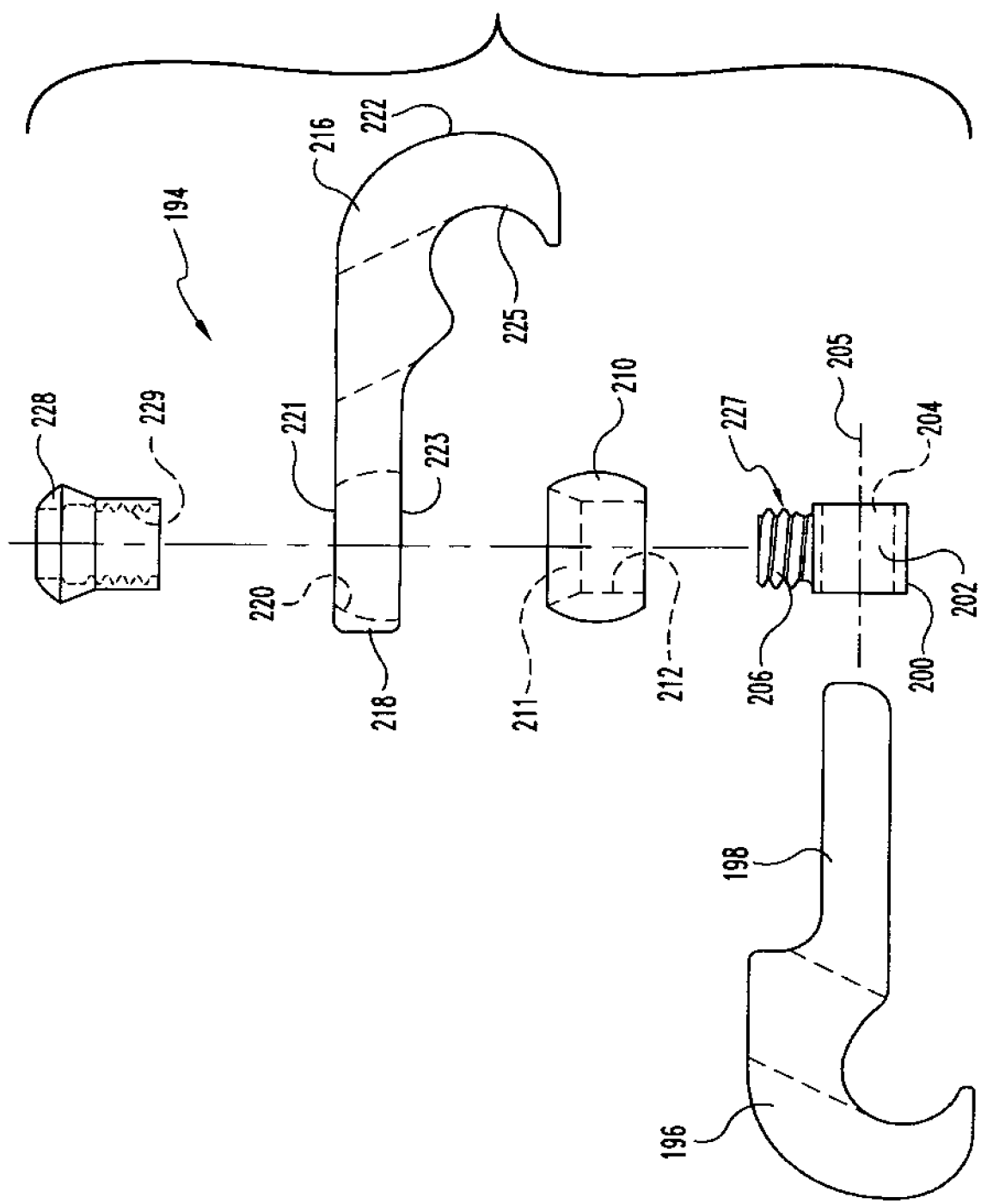

MULTI AXIAL CROSS LINK CONNECTOR SYSTEM FOR SPINAL IMPLANTS

CROSS-REFERENCE TO RELATED APPLICATIONS

The present application is a continuation of co-pending U.S. patent application Ser. No. 10/695,067 filed on Oct. 28, 2003, which claims the benefit of U.S. Provisional Application Ser. No. 60/421,701 filed on Oct. 28, 2002, the contents of each of these applications hereby incorporated by reference in its entirety.

BACKGROUND OF THE INVENTION

In general, the present invention relates to a system and components for correcting spinal defects. More specifically, the present invention is directed to spinal fixation systems including spinal rods and spinal rod interconnecting assemblies to treat and correct spinal deformities.

Spinal fixation systems are implanted during a surgical procedure to treat a variety of problems. These treatments include correction of congenital spinal deformities, e.g., scoliosis, spondylolisthesis, kyphosis, lordosis, and arthropathy; repair of spinal injuries; and fusion of vertebrae to stabilize congenital conditions and/or alleviate chronic lower back pain. Several techniques and systems have been developed for correcting and stabilizing the spine and facilitating spinal fusion.

In one common system, a longitudinal member such as a bendable rod, or spinal rod, is disposed along the vertebral column and is fixed at selected points to various vertebra along the length of the column by any number of fixation elements. A variety of these vertebral fixation elements are known and include hooks and bone screws. These fixation elements are configured to engage and attach to specific portions of the vertebrae. Usually, the surgeon attaches a vertebral fixation element to the spine in an appropriate anatomical position and then attaches each vertebral fixation element to the spinal rod. In conjunction, the surgeon twists and/or realigns the spinal column and/or individual vertebra to provide the desired treatment for the spinal defect. Consequently, the spinal rods may be bent or orientated along the spinal column non-parallel to each other.

The spinal rods are typically connected together to provide a more rigid support and alignment system, much like a ladder with rungs running between the supports. The cross-connecting members should accommodate the different orientations of the spinal rods. Further, the connecting members should be able to bridge the gap between the spinal rods without interfering with the structures and nerves, e.g., the spinal cord and/or spinal processes associated with or adjacent to the spinal column. Additionally, the connecting member should rigidly and securely interconnect the spinal rods. Obviously, failure of the system and dislocation of the spinal rods and associated components can cause the patient great pain and require additional surgical procedures to correct. An adjustable yet rigid cross connector would facilitate treatment of spinal defects.

Any surgical operation, by nature, is a delicate procedure; operations proximate to the spinal column are even more delicate and demanding. In addition to the expected surgical procedures, the surgeon must force the spinal column and individual vertebra into alignment. During this procedure or immediately thereafter, the surgeon must position the fixation elements, assemble the spinal rod system, secure the spinal rod system to the vertebrae, and then tighten the connections in the entire system so no further movement occurs. Assembly of the spinal rod system can be very difficult, especially when the components are coated with body fluids. A more "user friendly" spinal fixation system that could be assembled quickly and reliably in the operating room would be a great benefit to both surgeons and their patients.

Thus, in light of the above-described problems, there is a continuing need for advancements in the relevant field, including improved spinal fixation assemblies, related components, and methods for treating spinal defects. The present invention is such an advancement and provides a wide variety of benefits and advantages.

SUMMARY OF THE INVENTION

In general, the present invention provides an assembly and apparatus for treatment of spinal defects. The assembly can comprise elongate members, such as spinal rods, bone fasteners to secure the elongate members to anatomical positions on individual vertebral bodies, and cross-connectors to interconnect the elongate members.

In one form, the present invention provides an interconnector assembly that includes a first spinal rod connector, a second spinal rod connector, and an interconnector element to secure the two spinal rod connectors at a selected orientation relative to each other. The first and second spinal rod connectors can be formed with curved shafts to provide increased clearance for the spinal column. The interconnecting element can include a body having an aperture and a threaded stud extending from the body. In one form, the element can be provided as an eyebolt with an opening through which a portion of one or both of the rod connectors can extend. A fastener can be secured to the stud extending from the body to securely lock the first and second elongate members in a desired orientation relative to each other.

In other forms, the present invention provides an interconnecting member that includes a first shaft, a second shaft, and a plurality of fasteners. The second shaft can carry a interconnection body on its terminal end. The interconnection body can include an opening to receive a portion of the first shaft to the first connector. One of the fasteners can be secured to the body to lock the first spinal rod connector in a desired orientation relative to the second spinal rod connector.

In yet another form, the present invention provides a multi-axial variable interconnector that can interconnect two spinal rod connecting members. In one embodiment, the multi-axial spinal rod connector includes a ball and socket joint.

In other forms, the interconnecting element can be provided as an eyebolt. The eyebolt includes a body having an opening therethrough, an upper surface, and a stud extending from that surface. Additionally, the upper surface can include a plurality of radial splines positioned about the studs. Alternatively, a washer with an upper surface having a plurality of radial splines can be provided around the internal stud. In either form, a second spinal rod connector member can include a lower surface having splines configured to matingly engage with the splines about the stud. A fastener can be secured to the stud to interdigitate the splines and, consequently, lock the first spinal rod connector in a desired orientation relative to the second spinal rod connector.

In still yet other forms, the present invention provides a spinal rod connector member that can secure a spinal rod within a hook. The hook can include a saddle or ridge portion within the curved or concave portion of the hook. The ridge or saddle portion can allow the spinal rod to seat within the hook at various orientations. Additionally, the spinal rod connector can include a threaded aperture and a fastener to be received therein to secure the spinal rod within the hook.

In still yet other forms, the present invention provides a pre-assembled interconnection assembly. The pre-assembled interconnection assembly maintains restricted movement of a first and second spinal rod connecting member. The restricted movement of the first and second spinal rod connecting members can be provided to allow extension of the interconnecting member and/or rotation of one spinal rod connecting member relative to a second spinal rod connecting member to secure non-parallel spinal rods. The restricted movement can also inhibit inadvertent disassembly of the interconnection assembly. Additionally, the connecting element can be configured to minimize or eliminate contact with various bone and neural structures, processes located posteriorly of the spinal column, while rigidly securing a pair of spinal rods extending longitudinally with the spinal column.

Further objects, features, forms, and advantages of the present invention will become apparent from the following descriptions and drawings contained herein.

BRIEF DESCRIPTION OF THE DRAWINGS

FIG. 12 is a perspective view of a connector assembly including the female connector of FIG. 10 and the interconnecting element of FIG. 11 in accordance with the present invention.

FIG. 13 is an exploded view of another embodiment of a connector assembly having a variable angle interconnection in accordance with the present invention.

FIGS. 14, 14a, and 14b illustrate an insert for use in the variable angle interconnection of FIG. 13.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described systems, connection components, and methods, and any further applications of the principles of the invention as described herein, are contemplated as would normally occur to one skilled in the art to which the invention relates.

Figure 1:
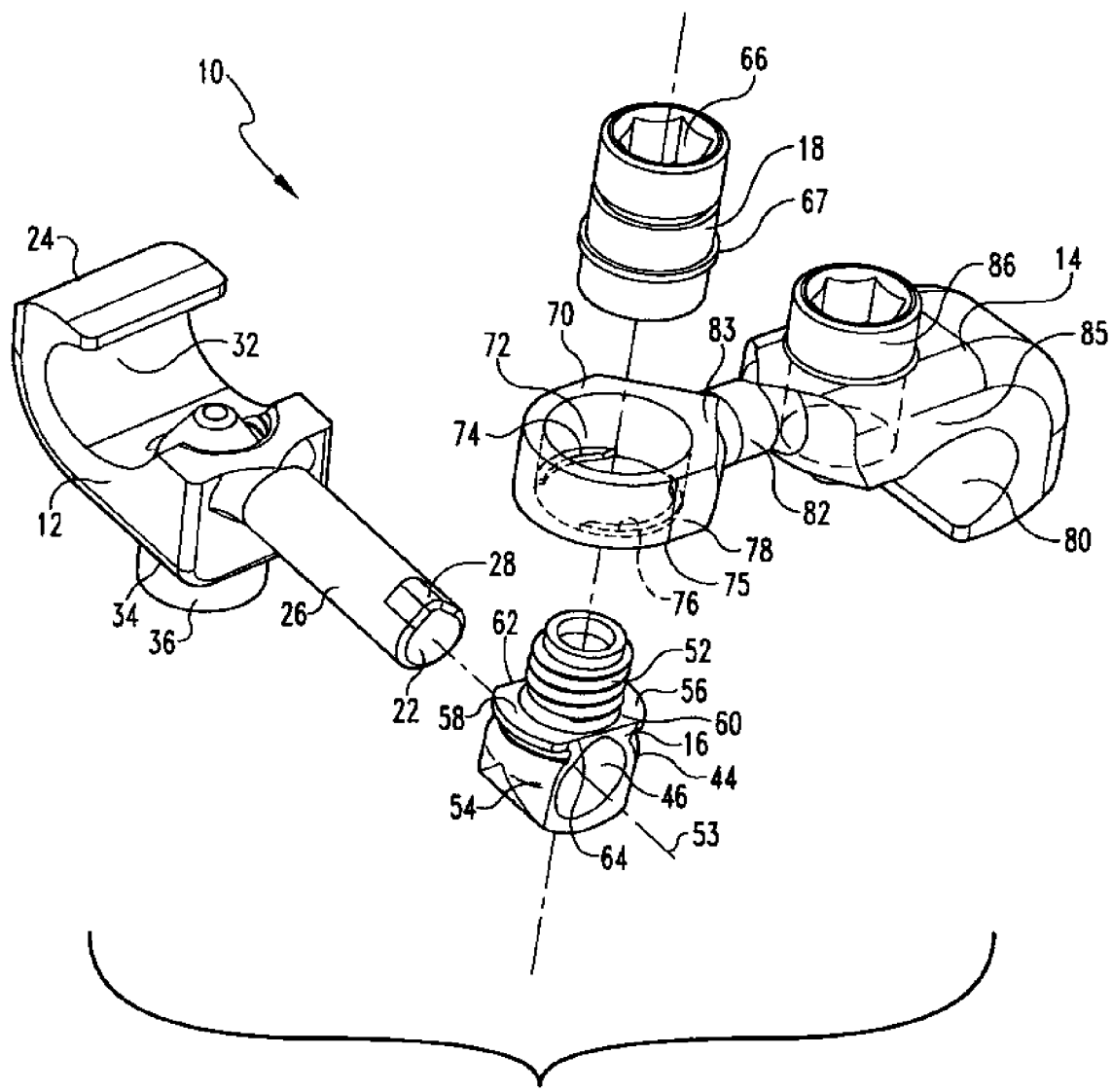
FIG. 1 is an exploded, perspective view of one embodiment of a spinal rod connector assembly in accordance with the present invention.

FIG. 1 is an exploded, perspective view of one embodiment of a connector assembly 10 in accordance with the present invention. Connector assembly 10 includes a male connector member 12, a female connector member 14, an interconnecting element 16, and fastener 18. Male connector member 12 includes a proximal end 22, an opposite distal end 24, and a shaft 26 therebetween. Proximal end 22 is provided to exhibit a round or oval cross-sectional profile. In a preferred embodiment, a protuberance or projection 28 extends from proximal end 22. In the illustrated embodiment, projection 28 is provided as a cam or a lobe extending substantially orthogonal to a longitudinal axis or direction defined by shaft 26. In alternative embodiments, projection 28 can be provided as a single or multiple finger(s) or spline(s) extending orthogonal or obliquely from shaft 26.

Shaft 26 is provided as a cylindrical shaft, although it should be understood that shaft 26 can be provided in any configuration as desired. For example, shaft 26 can be provided with an oblong, rectangular, or triangular cross-section profile. Shaft 26 is illustrated as a substantially straight elongate member defining a longitudinal axis. In other embodiments, shaft 26 can be formed as an arched or curved shaft. Shaft 26 carries a rod connecting portion 32 on its distal end 24. In any of the embodiments, shaft 26 can have a relative smooth exterior or, alternatively, its exterior can be roughened or knurled.

Shaft 26 terminates in rod connecting portion 32, which is configured to engage a spinal rod or another elongate member, or a bone fastener. In a preferred embodiment, portion 32 is provided with a channel, recess or a hook, as desired, each which are adapted and configured to, at least partially, encircle a spinal rod.

Additionally, an aperture 34 or bore with internal threads can be tapped into male connecting member 12 to secure the member to a spinal rod or bone fastener. Aperture 34 extends into distal end 24 and preferably through shaft 76 or distal end 24 and into the interior of the hook. Aperture 34 can be formed into shaft 26 either orthogonal to or at an angle oblique to the longitudinal axis defined by shaft 26. For example, aperture 34 can extend from an exterior surface of portion 32 to an interior surface proximal to the internal crook or hook of rod connecting portion 32. A threaded fastener 36 can be threadedly received within aperture 34 to secure an included spinal rod to male connector member 12. Examples of threaded fasteners are illustrated in U.S. Pat. Nos. 5,947,966 and 6,193,719, which are incorporated by reference in their entirety. Fastener 36 can include a blunt or concave tip. Alternatively, fastener 36 can include a tip that includes teeth and/or cutting edges to engage and indent a portion of an included spinal rod (not shown).

In a preferred embodiment, male connector member 12 is provided to have a preferred length selected for a particular application or use. In one embodiment, the preferred length measured along the longitudinal axis defined by shaft 26 of between about 20 mm and about 46 mm.

Interconnecting element 16 is illustrated as an eyebolt 44. Eyebolt 44 includes an aperture 46 extending through a cylindrical or circular body 54. Aperture 46 is provided to receive a portion of a shaft from a connecting member, such as connecting member 12 therethrough. In the illustrated embodiment, aperture 46 is configured as an oblong or oval opening. Preferably, aperture 46 is provided to matingly receive proximal end 22 including projection 28 of male connector member 12. Interconnecting element 16 also includes a threaded stud 52 extending from body 54 substantially orthogonal to an axis 53 defined by aperture 46.

In one embodiment, an interlocking member 56 is disposed between body 54 and threaded stud 52. In the illustrated embodiment, interlocking member 56 includes a pair of flanges or shelves 58 and 60 extending diametrically opposite each other circumferentially about body 54. Disposed between shelves 58 and 60 are a pair of opposing lands or truncated portions 62 and 64, e.g., truncated when compared to shelf portions 58 or 60. Truncated portions 62 and 64 can be formed substantially flush with the lateral sides of body 54. The shelves 58 and 60 are provided as part of the swage locking mechanism to interengage interconnecting element 16 with female connector member 14.

In another embodiment, threaded stud 52 extends directly from eyebolt 44 without the interlocking member 46 interposed therebetween.

Female connector member 14 is provided as the counterpart portion to male connector member 12. Connector member 14 includes a proximal portion 78, a distal spinal rod engaging portion 80, and a shaft 82 therebetween. Shaft 82 can have a relative smooth exterior or, alternatively, its exterior can be roughened or knurled. Spinal rod engaging portion 80 can be provided substantially as described for rod connecting portion 32 of male connecting member 12. In a preferred embodiment, portion 32 is provided with a channel, recess or a hook, as desired, each which are adapted and configured to, at least partially, encircle a spinal rod. Additionally, an aperture 85—similar to aperture 34—can be provided to extend either orthogonal or obliquely through member 14. Preferably, aperture 85 allows a threaded fastener to engage the outer surface of a spinal rod seated within the hook or crook of rod engaging portion 80. A fastener such as fastener 86 can be threadedly engaged through aperture 85 to secure a spinal rod in portion 80.

Female connector member 14 includes a body 70 having an aperture 72 therethrough. In one form, body 70 is a substantially circular or oval configuration. In other forms, body 70 can be provided as desired, for example, cuboid or trapezoid. Aperture 72 is configured to slideably receive stud 52 therein. In preferred embodiments, aperture 72 is configured to have a larger internal diameter than the external diameter of the external threads on stud 52. Consequently, in a preferred embodiment, the inside surface of aperture 72 is a smooth bore without any threads. In alternative embodiments, the internal surface of aperture 72 can be a threaded bore. In yet another embodiment, the internal surface of aperture 72 includes a pair of internal shelves 74 and 76. Preferably shelves 74 and 76 are positioned diametrically opposite each other proximate to the lower surface 75 of body 70. Shelves 74 and 76 are configured to interengage with interlocking member 56 and/or shelves 58 and 60 to secure female connector member 14 with interlocking member 56. (For example, see FIG. 3.) In still yet other embodiments, aperture 72 can be provided as a smooth bore without either internal threads or internal shelves. Fastener 86 can be provided as described for fastener 36.

In a preferred embodiment, female connector member 14 is provided to have a desired length suitably selected such that in conjunction with member 12, two spinal rods can be secured together. In a preferred embodiment, connector member 14 is provided to have a length measured along the longitudinal axis defined by shaft 82 of between about 10 mm and about 65 mm.

Figure 2:
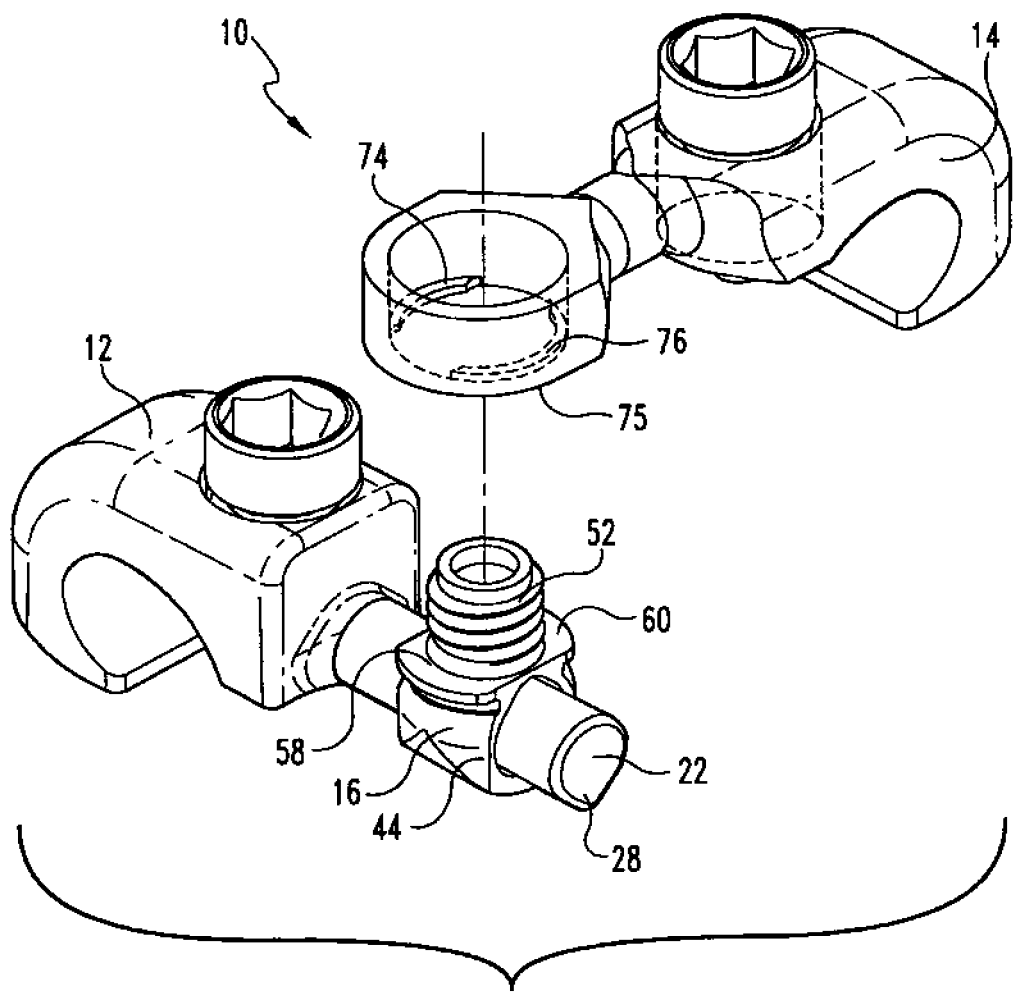
FIG. 2 is an exploded, perspective view of the connector assembly of FIG. 1, partly assembled.
Figure 3:
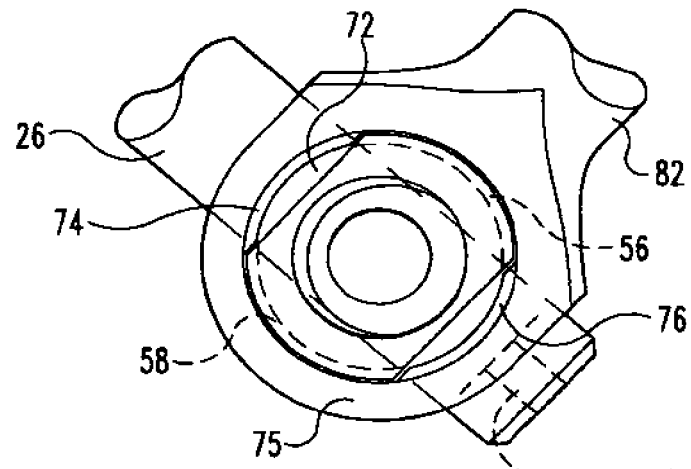
FIG. 3 is a partial, top-plan view of the connector assembly of FIG. 1, partly assembled.
Figure 4:
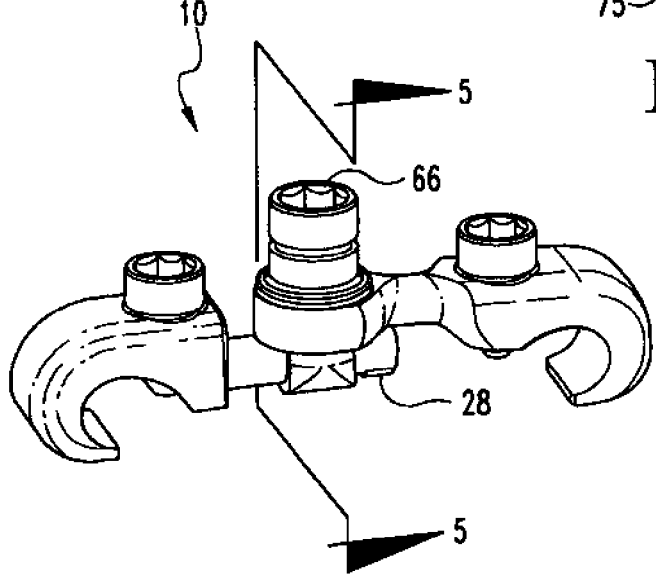
FIG. 4 is a perspective view of the connector assembly of FIG. 1 pre-assembled in accordance with the present invention.
Figure 5:
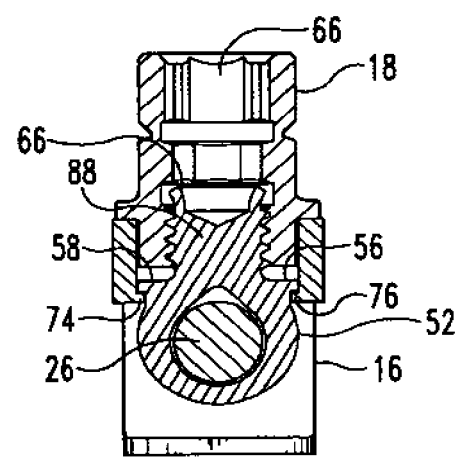
FIG. 5 is a cross-sectional view of the interconnecting element of the connector assembly of FIG. 1.

Referring additionally to FIGS. 2 through 5, in use, proximal end 22 of male connector member 12 is received into and through aperture 46 until proximal end 22 and projection 28 extend from the opposite side of interconnection element 16. When thus engaged, projection 28 is disposed on the opposite side of eyebolt 44 from distal end 24 of male connector member 12 as illustrated in FIG. 2. Rotation of male connector member 12 about its longitudinal axis allows projection 28 to contact the exterior surface of element 16 and be positioned adjacent lower surface 81 of eyebolt as illustrated in FIG. 4. It will be understood that to provide a variable angle connector, male connector member 12 can be rotated by an amount either less than or greater than about 180°. Next, female connector member 14 is positioned over stud 52 such that shelves 74 and 76 are proximal to truncated portions 62 and 64 as illustrated in FIG. 3. Rotation of female connector member 14 about stud 52 then engages shelves 74 and 76 with shelves 58 and 60. This prevents connecting element 16 from being inadvertently disengaged or removed from stud 52 (without counter rotation). It will be understood that female connector member 14 can be adjusted at any angle in relation to male connector member 12 and/or interconnecting element 16 as desired to secure the spinal rods and facilitate treatment. Thereafter, fastener 18 can be engaged with stud 52 to secure male connector member 12 and female connector member 14 in the desired orientation as illustrated in FIG. 5.

In one embodiment, fastener 18 includes internal threads to engage the external threads on stud 52. Additionally, fastener 18 can be provided as a setscrew with an internal tool engaging recess or imprint. In this embodiment, at least a portion of aperture 72 has a diameter sufficient to receive a portion or all of fastener 18 therein. This embodiment can minimize the profile of the assembled connector that extends posteriorly from the site of implantation. Additionally, the interior bore of aperture 72 can include a step or groove which can contact and bear against a corresponding (mating) portion on fastener 18. Consequently, threading fastener 18 on stud 52 forces body 70 of the female connector member 14 onto eyebolt 44 such that lower surface 81 of body 70 contacts a portion of shaft 26 and/or projection 28. Securing fastener 18 to stud 52 forces projection 28 to overhang a portion of body 70 and, consequently, inhibits withdrawal of shaft 26 of male connector member 12. In other embodiments, fastener 18 includes a lip 67 that extends about its outer perimeter. When fastener 18 is threaded on stud 52, lip 67 contacts the upper surface 83 of body 70 and similarly frictionally engages body 70 with shaft and/or projection 28. In one form of this embodiment, fastener 18 can be provided as a cap having a round top. In either embodiment, male connector member 12 and interconnecting element 16 are locked or secured into a desired orientation relative to each other.

A variety of fasteners 18 can be used with the present invention. For example, one fastener, referred to as a "break off set screw", can include a weakened section to allow a portion of fastener 18 to break or shear off upon application of sufficient torque. Examples of such break off set screws are described in U.S. Pat. No. 6,478,795 issued to Gournay et al. which is incorporated herein by reference.

Figure 6A:
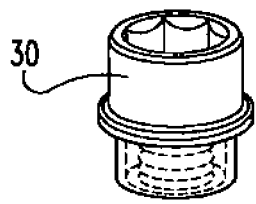
FIGS. 6A and 6B are perspective views of alternative fasteners for use with the present invention.

FIG. 6A provides another illustrative embodiment of a fastener 30 for use with the present invention. Fastener 30 includes an imprint configured to receive a driving tool. The imprint configuration can be provided as desired including a hex head imprint, a four-sided imprint, or a "torq" imprint sized as desired.

Figure 6B:
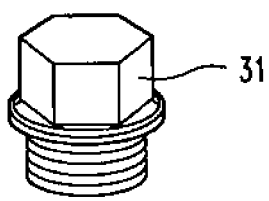

FIG. 6B illustrates yet another embodiment of a fastener 31 for use with the present invention. Fastener 31 includes a head configured to be grasped by a driving tool such as a six-sided socket. Any of fasteners 18, 30, and 31 can include internal threads or external threads to engage a stud extending from an eyebolt.

It should also be understood that connector assembly 10 can be provided by the manufacturer as an assembled unit—albeit loosely connected. When thus provided, the components cannot be inadvertently separated from each other. In one form, as illustrated in FIG. 5, the interior portion of stud 52 includes an interior bore 88 and fastener 18 includes a through bore. During manufacture, a dam (not shown) is inserted into interior bore 88 after attachment of fastener 18. The dam can then splay the end 66 of interior bore 88 to prevent fastener 18 from backing off the threaded stud 52. This prevents the assembly, including male connector member 12, female connector member 14, and interconnecting element 16, from becoming inadvertently separated.

Figure 7:
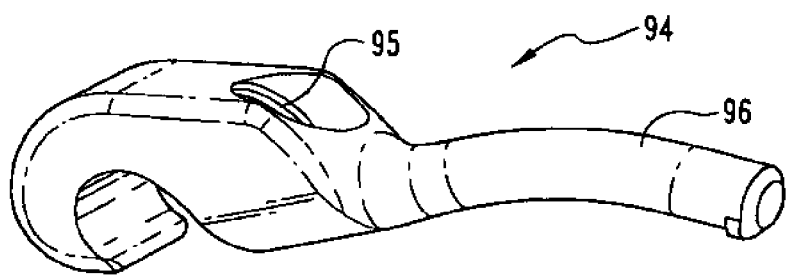
FIG. 7 is a perspective view of a male connector member having a curved shaft in accordance with one embodiment of the present invention.

FIG. 7 is a perspective view of an alternative embodiment of a male connector member 94. Member 94 is provided as has been described for male connector member 12. However, male connector member 94 includes an arched or curved shaft 96. Member 94 can be provided with an curved or arched side profile selected to eliminate contact between the resulting connector assembly and the spinal processes on the posterior of the spinal column. (See, for example, FIG. 9.)

Furthermore, connector member 94 includes a threaded aperture 95 that extends therethrough at an angle oblique to shaft 96.

Figure 8:
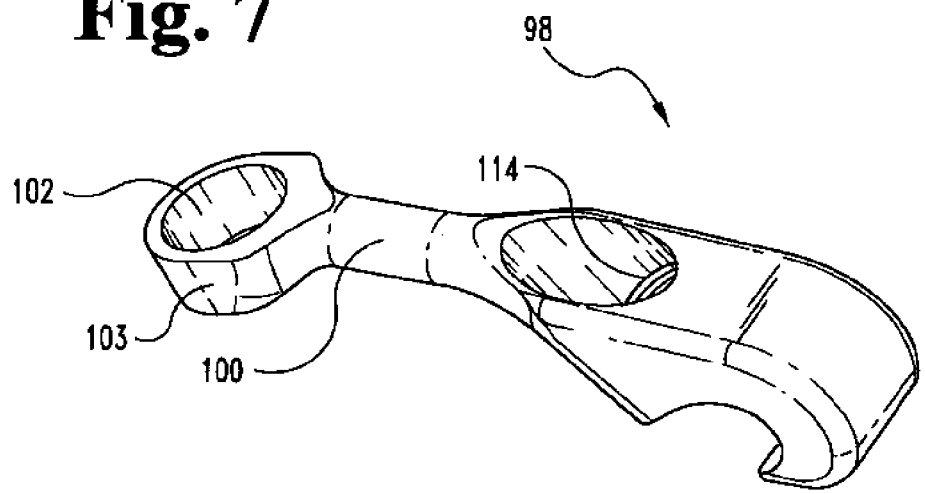
FIG. 8 is a perspective view of a female connector member having a curved shaft in accordance with one embodiment of the present invention.

FIG. 8 is a perspective view of a female connector member 98, similar to female connector member 14. Connector member 98 includes a curved shaft 100. Shaft 100 can be formed to have a curved or arched configuration that is selected to minimize or eliminate contact between the resulting connector assembly and the spinal processes on the posterior of the spinal column. Additionally, shaft 100 can be provided with substantially the same curvature as that of shaft 96.

Female connector member 98 includes a body 103 having an aperture 102 therethrough. Aperture 102 is sized and configured to receive a stud such as stud 52 on eyebolt 44. In the embodiment illustrated in FIG. 7, aperture 102 is provided as a substantially smooth bore without any threads or interlocking shelves or the like. Additionally, member 98 includes a threaded bore 114 provided as discussed above for aperture 95 in male connector member 94.

Figure 9:
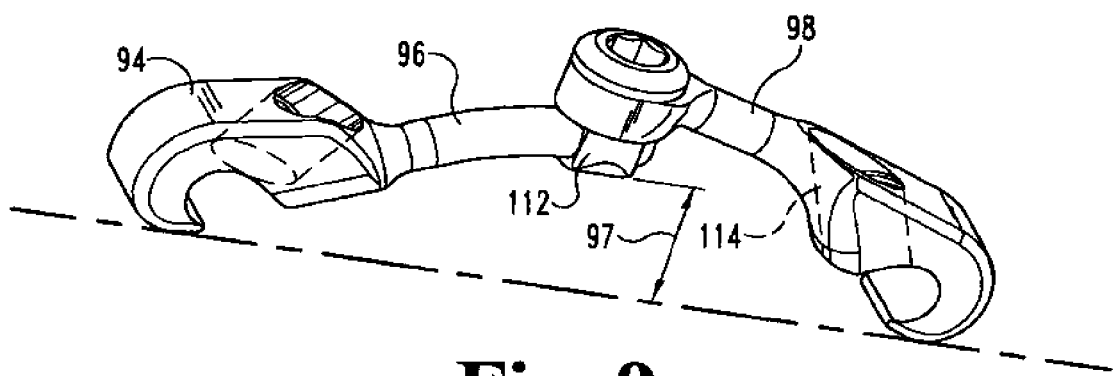
FIG. 9 is a prospective view of a connector assembly having curved connector members in accordance with one embodiment of the present invention.

FIG. 9 is a perspective view of a connector assembly 110. Assembly 110 includes male connector member 94, female connector member 98, and an interconnecting element 16 secured with fastener 18. In the illustrated embodiment, male connector member 94 and female connector member 98 are formed to exhibit the same or substantially similar arched profile along their respective shafts. Further, the overall length of assembly 110 measured along a longitudinal axis defined by the shaft of female connector member 98 can be variable by either sliding shaft 96 further through eyebolt 112 or sliding shaft 96 in the opposite direction to withdraw it from eyebolt 112. Loosening fastener 18 allows shaft 96 of male connector member 94 to slide through the aperture 46 in interconnecting element 16. Consequently, the overall length of connector assembly 110 can vary to allow the distal ends of the respective male and female connector members to grasp spinal rods positioned proximate to the transverse processes of the vertebra. Connector assembly 110 can have a depth measured along reference line 97 sufficient to minimize any contact between either male connector member 94 or female connector member 98 and the spinous processes.

Figure 10:
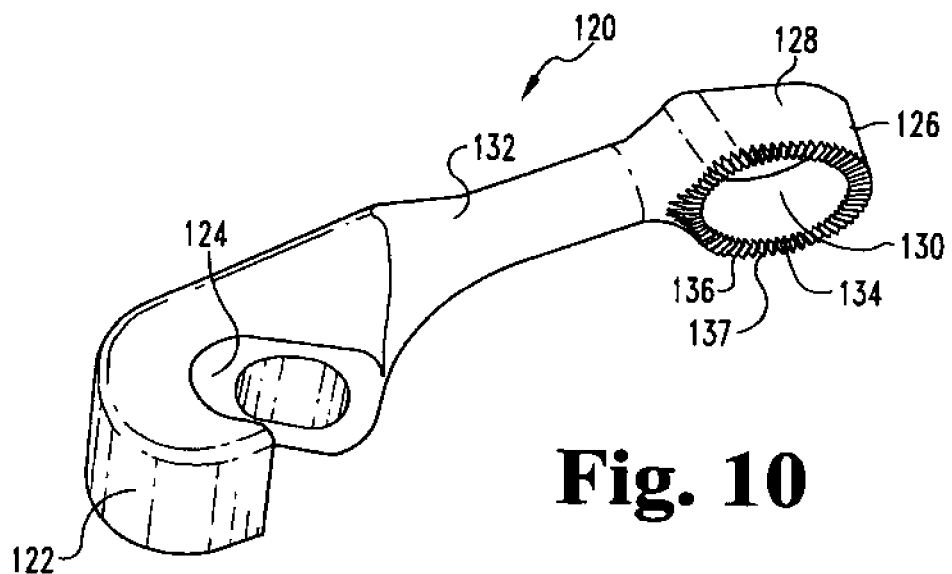
FIG. 10 is a perspective view of one embodiment of a female connector member having radial splines on a contacting surface in accordance with another embodiment of the present invention.

FIG. 10 is a perspective view of another embodiment of a female connector member 120 in accordance with the present invention. Female connector member 120 is formed similarly to female connector member 14 or connector 98. Connector member 120 includes a distal end 122 defining a rod securing portion 124, a proximal end 126, and a shaft 132 therebetween. Proximal end 126 carries a body 128 with an aperture 130 therethrough. Body 128 includes a lower surface 134 having a number of radial splines or alternating ridges 136 and grooves 137 positioned circumferentially about aperture 130. Ridges 136 and grooves 137 are provided to facilitate securing or locking female connector member 120 in a desired orientation.

Shaft 132 is disposed between distal end 122 and proximal end 126. In the illustrated embodiment, shaft 132 is provided as an arched shaft similar to shaft 100 on female connector member 98. In other embodiments, shaft 132 can be provided as a straight shaft such as shaft 82 in FIG. 1. Furthermore, shaft 132 can be provided to have any desired cross-sectional configuration, including round, oval, rectangular, and the like. In still alternative embodiments, shaft 132 can be provided as a plate having a substantially uniform cross section, e.g., a rectangular cross section extending from proximal end 126 to distal end 122.

Figure 11:
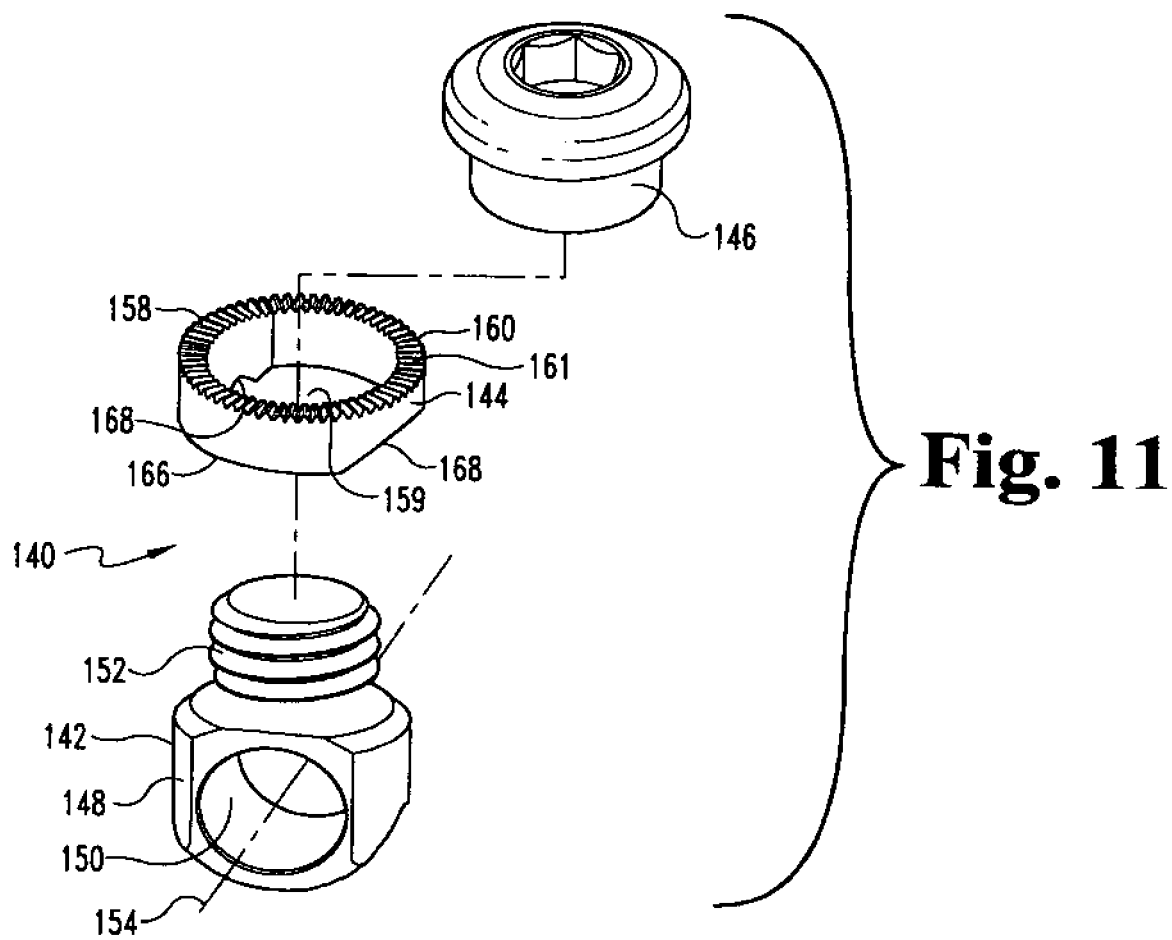
FIG. 11 is an exploded view of an interconnecting element including interlocking splines in accordance with another embodiment of the present invention.

FIG. 11 is an exploded view of an alternative embodiment of an interconnecting assembly 140 for use in the present invention. Interconnecting assembly 140 includes eyebolt 142, a washer body 144, and a fastener 146.

Eyebolt 142 includes a lower body 148 having an aperture 150 extending therethrough. A threaded stud 152 extends upwardly from body 148 substantially orthogonal to the central axis 154 of aperture 150.

Washer body 144 includes an upper surface 158, a lower surface 166, and an opening 159 therethrough sized to receive a portion of lower body 148. Upper surface 158 includes a plurality of ridges or radial splines 160 and grooves 161 positioned circumferentially around an opening 159. In a preferred embodiment, splines 162 are sized and spaced from each other to matingly engage with ridges 136 on female connector member 120 in FIG. 10. Lower surface 166 is positioned opposite upper surface 158. In a preferred embodiment, lower surface 166 is provided to bear against a shaft of a male connector member (not shown). In a preferred embodiment, lower surface 166 includes a recess 168, more preferably a pair of recesses diametrically opposed about opening 159. When secured with fastener 146, recess(es) 168 bear(s) against and contacts a shaft of an inserted male connector member and inhibits rotation of the male connector member about stud 152 relative to the included female connector member.

FIG. 12 is a perspective view of a connector assembly 174 having splined locking surfaces in accordance with the present invention. Connector assembly 174 includes a male connector member 176, a female connector member 178, and interconnecting element 180. Male connector member 176 can be provided substantially as has been described for member 94. Female connector member 178 can be provided substantially as has been described for member 140. Similarly, interconnecting element 180 can be provided substantially as has been described for element 120. It can be observed in the illustrated embodiment that female connector member 178 is rotatable about an axis 181 defined by fastener 182 to any desired orientation relative to male connector member 176. When the surgeon has positioned either connecting member 178 or 176 in a desired orientation, the surgeon can then tighten fastener 182 to interdigitating splines 184 and 186 to securely lock the two members in the desired orientation.

FIG. 13 is an exploded view of another embodiment of a connector assembly in accordance with the present invention. Connector assembly 194 includes a male connector member 196. Male connector member 196 can be provided substantially as has been described for male connector member 12. In alternative embodiments, member 196 can be provided with an arched shaft as described for connector 94. As noted before, the shaft can be provided with a variety of cross-section profiles. Connector assembly 194 also includes an interconnection element 200. Interconnection element 200 is provided as an eyebolt 202 with an aperture 204 formed therein and a stud 206 extending substantially orthogonal to the central axis 205 of aperture 204. Eyebolt 202 can be provided substantially as described for eyebolt 44.

Assembly 194 also includes a washer or an insert 210 to be slideably received on stud 206. In the illustrated embodiment, insert 210 is configured as a substantial cylindrical washer having a partial spherical cross section. Insert 210 also includes an internal bore 212 dimensioned and configured to be received over stud 206 and, optionally, an upper portion of eyebolt 202.

Referring additionally to FIGS. 14, 14a, and 14b, insert 210 is illustrated for use in assembly 194. FIG. 14 is a side elevation view. FIG. 14a is a cross-section view taken along section line 14-14, and FIG. 14b illustrates the lower surface 230 of insert 210. It can be observed that lower surface 230 includes recesses 232 and 234. Recesses 232 and 234 are provided to bear against and contact a portion of shaft 198 of male connector member 196. In addition or in the alternative, insert 210 includes a slit 236 formed in its side wall 238. Slit 236 allows insert 210 to vary in dimension, if necessary, to receive stud 206 within bore 212. Additionally, slit 236 can allow insert 210 to deform and frictionally engage one or more of stud 206, female connector member 216, and male connector member 196 to eyebolt 202. Insert 210 can be formed of a biocompatible material including surgical steel, stainless steel, titanium, a ceramic, a composite, a deformable, and/or a flexible material such as a polymeric material—preferably an elastic polymeric material.

Referring specifically to FIG. 13, female connector member 216 includes a proximal end 218 having an bore or aperture 220 formed therein, a distal end 222 defining a rod securing portion 225, and a shaft therebetween. Aperture 220 adjacent proximal end 218 is configured to receive insert 210. In one form, aperture 220 is sized and configured as a socket with the insert designed as the "ball" of a ball and socket joint. In another form, aperture 220 has a smooth cylindrical bore having a substantially uniform internal diameter throughout. In yet other forms, aperture 220 has a bore with an internal diameter that is greater than the diameter of one or more of the openings 221 or 223 leading into the interior portion of aperture 220. The larger internal diameter is sized to matingly engage or receive insert 210 therein. In this form, female connecting member 216 can pivot about insert 210, which is disposed within the internal bore of aperture 220.

The distal end of female connector member 216 defines a rod securing portion. Additionally, distal end 222 includes a threaded aperture 226. In a preferred embodiment, the rod securing portion includes a hook and the threaded aperture 226 extends from an upper surface on female connector member 216 into the crook portion of hook 224.

Fastener 228 is provided to threadedly engage with stud 206. In a preferred embodiment, stud 206 includes external threads 227, and fastener 228 contains internal threads 229 configured to matingly engage with the external threads 227 of stud 206. Additionally, fastener 228 has an external dimension or diameter selected to be at least partially received within aperture 220 and, optionally, within a portion of the internal recess 211 of insert 210.

In use, shaft 198 of male connector member 196 is received within aperture 204 of the eyebolt 202. Thereafter, insert 210 is positioned over stud 206 in contact with a portion of shaft 198. Female connector member 216 is then engaged to or forced over insert 210. In this fashion, insert 210 is received within the aperture 220 of female connector member 216. Fastener 228 then engages with stud 206 to initially assemble the connector assembly—albeit while allowing the male and female connector members 196 and 216 restricted movement, both to extend the length of the resulting assembly and the relative orientation of the male and female connector members 196 and 216 to each other. It will be observed from the illustration in FIG. 12 that female connector member 216 can move or rotate about an axis defined by stud 206 and pivot along or in line with that same axis. Additionally, it can be observed that when insert 210 is provided with a hemispherical cross section, female connector member 216 can pivot about multiple axes. Consequently, a surgeon can position the male and female connector members 196 and 216 to circumvent contacting the neural structures or processes along the spinal column.

Securing fastener 228 tightly onto stud 206 forces the insert 210 to expand and frictionally engage the internal portion of aperture 220 and optionally stud 206. This in turn locks the male connector member 196 within aperture 204 and prevents female connector member 216 from movement relative to male connector member 196 and/or interconnection element 200.

Figure 15:
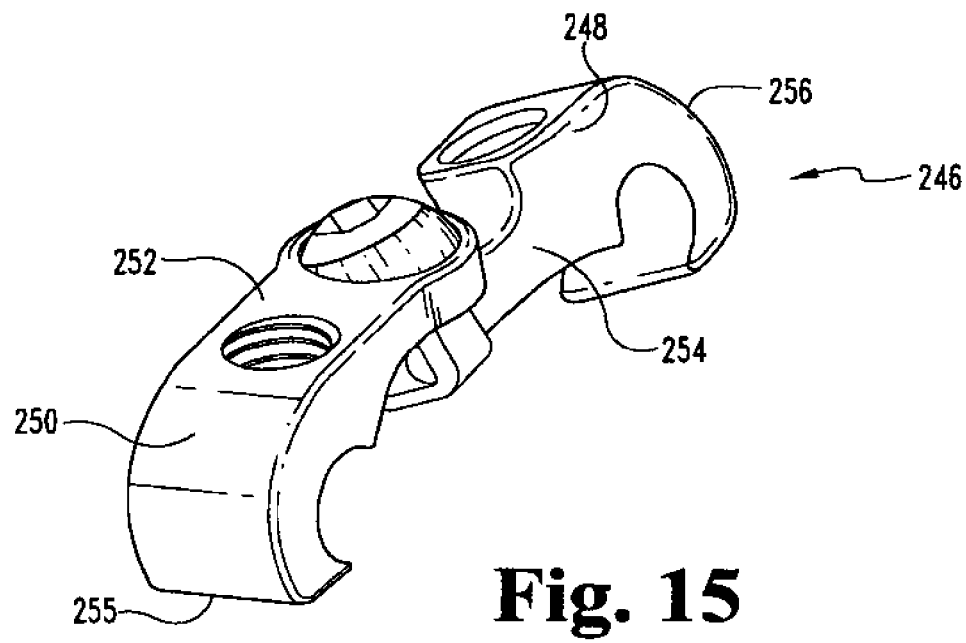
FIG. 15 is a prospective view of the connector assembly of FIG. 13.

FIG. 15 is a perspective view of another embodiment of a connector assembly 246 in accordance with the present invention. Connector assembly 246 is provided substantially as has been described for connector assembly 194 in FIG. 13. However, as can be seen from the illustration, female connector member 248 and male connector member 250 include a plate 252 and 254, respectively, in lieu of cylindrical shafts extending to the proximal end to the distal end of the respective members. Furthermore, it can be seen from the illustration that female connector member 248 is provided at an angle and is non-planar with male connector member 250. In this configuration, connector assembly 246 can secure two elongate members. The two secured elongate members need not be positioned parallel nor lie in the same plane with each other. When viewed along a longitudinal axis defined by the elongate female connector member 248, the connector assembly appears to twist from a first end 255 to a second end 256. This can allow a surgeon to exert the desired force and direction on a particular vertebra to correct various spinal deformities.

Figure 16:
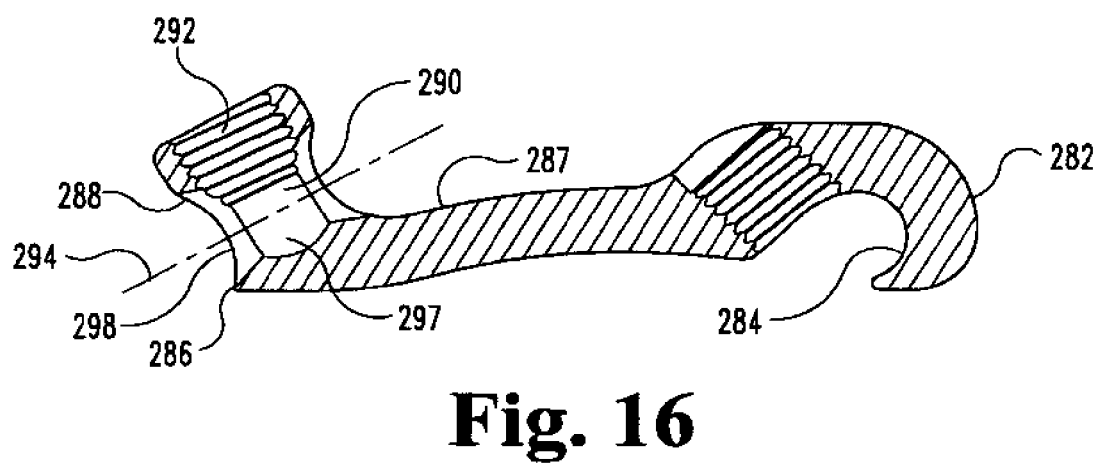
FIG. 16 is a cross-sectional view of a one-piece female connector member having an interconnecting element in accordance with the present invention.

FIG. 16 is a cross-sectional view of yet another embodiment of a female connector member 280 for use in the present invention. Member 280 includes a shaft 281 disposed between distal end 282 and proximal end 286. Distal end 282 defines a spinal rod connecting portion 284. Rod connecting portion 284 can be configured substantially as described for portion 32 in FIG. 1. Proximal end 286 carries an interconnector body 288. Interconnecting body 288 includes an aperture 290 extending therethrough and defining a central axis 294. Axis 294 is positioned to lie substantially in the same plane as shaft 281. Aperture 290 is provided to receive an insert such as an insert described above; for example, insert 210. In this embodiment, female connector member 280 is provided as a one-piece unit including the interconnecting body.

Aperture 290 is provided as a cylindrical or oval bore. In selected embodiments, aperture 290 need not have a constant or uniform diameter throughout. Preferably, aperture 290 is provided with enlarged openings 296 and 298. Further, central portion 297 of aperture 290 is sized and configured to receive an insert, such as inset 210 of FIG. 14.

Additionally, body 288 includes a threaded opening 292 disposed to lie about an axis positioned substantially orthogonal to the axis 294 of aperture 290. Opening 292 is provided with a threaded interior surface to threadedly receive a fastener such as fastener 36 in FIG. 1.

Figure 17:
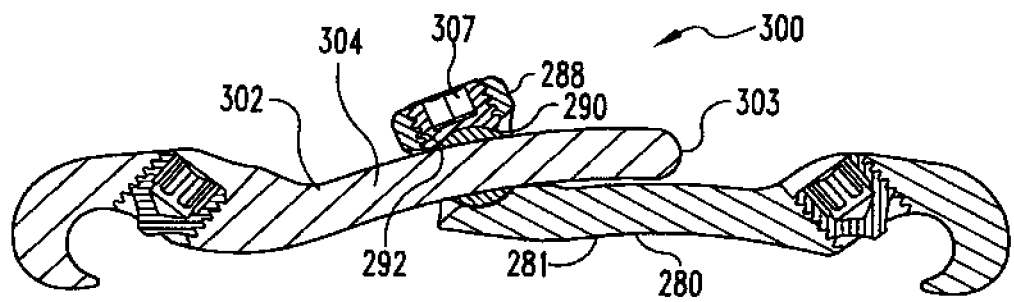
FIG. 17 is prospective view of a connector assembly including the female connector member of FIG. 16.

FIG. 17 is a cross-sectional view of a connector assembly 300. Connector assembly 300 includes female connector member 280 and male connector member 302. Male connector member 302 includes a proximal end 303 and shaft 304 that are sized and configured to be received within aperture 290 of interconnecting body 288. Additionally, an insert such as an insert that has been described in FIGS. 13, 14, 14*a*, and 14*b* can be included in the aperture of the interconnecting body. In a preferred embodiment, proximal end 303 is slideably received within the internal bore 212 of insert 210 and through aperture 290 of interconnecting body 288. In this embodiment, shaft 304 and shaft 281 nest together. Preferably each of shaft 304 and 281 has approximately the same curvature and cross-sectional dimensions. Since aperture 290 is provided with enlarged openings 296 and 298, as discussed above, male connector 302 can pivot about the central portion 297 of aperture 290. Consequently, female connector 280 and male connector 302 can be adjusted to be aligned with each other or at an angle oblique (either laterally and/or vertically) to each other as desired. In use, the surgeon can adjust female connector 280 and male connector 302 to engage in spinal rods (not shown) that are parallel or non parallel with each other. Thereafter, a fastener 307 having external threads can be threadedly engaged within opening 292, locking the two components, i.e., the male connector 302 and female connector 280, in the desired orientation.

In a preferred embodiment, the individual components of connector assembly 300 can be assembled prior to surgery. The resulting assembly can be maintained as a single, adjustable unit allowing restricted movement of female connector member 280 relative to male connector member 302. This can greatly increase ease of use and facilitate implantation of the device.

Figure 18:
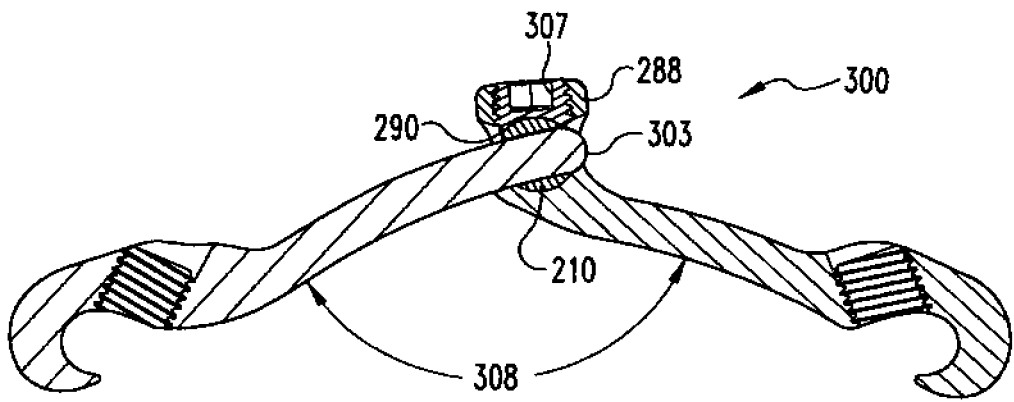
FIG. 18 is prospective view of the connector assembly of FIG. 17 in which the male and female connector members are orientated to position the interconnection element to allow for greater clearance for a spinal column.

FIG. 18 illustrates connector assembly 300 in a fully extended and/or arched (bent) configuration. Male connector member 302 has been positioned inside aperture 290 such that proximal end 303 is adjacent interconnection body 288. Consequently, connector assembly 300 can be adjusted to define an angle 308 (considering the relative orientation of shafts 281 and 304) of between about 100° and about 80°. After the surgeon has positioned the male connector and female connector as desired, fastener 307 can be tightened to lock the interconnection assembly to the desired orientation. It should be understood that interconnection assembly 300 can be secured to elongate members either before or after tightening fastener 307.

Figure 19:
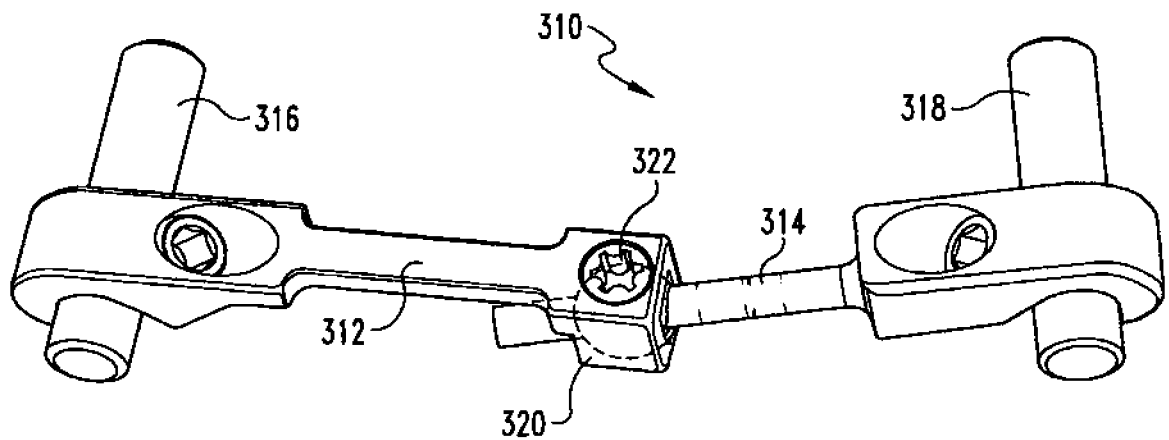
FIG. 19 is yet another embodiment of a connector assembly having a variable angle interconnection in accordance with the present invention.

Referring additionally to FIG. 19, there is shown another embodiment of an interconnector assembly 310. As has been described above, connector assembly 310 includes two connecting members, female connector member 312 and male connector member 314. Assembly 310 includes a ball and socket interconnection element 320. Interconnector element 320 can be provided as a substantially rectangular cross section with a fastener 322 seated within the internal portion of the element. This can provide a low-profile crosslinking element that does not extend posteriorly from the structures of the spinal column and associated processes.

A pair of elongate members 316 and 318 are illustrated secured to the interconnector assembly 310. One elongate member is secured to the distal ends of the connector members 312 and 314, respectively. It can be observed that elongate member 318 is not positioned to lie parallel to or in the same plane as elongate member 316.

Figure 20:
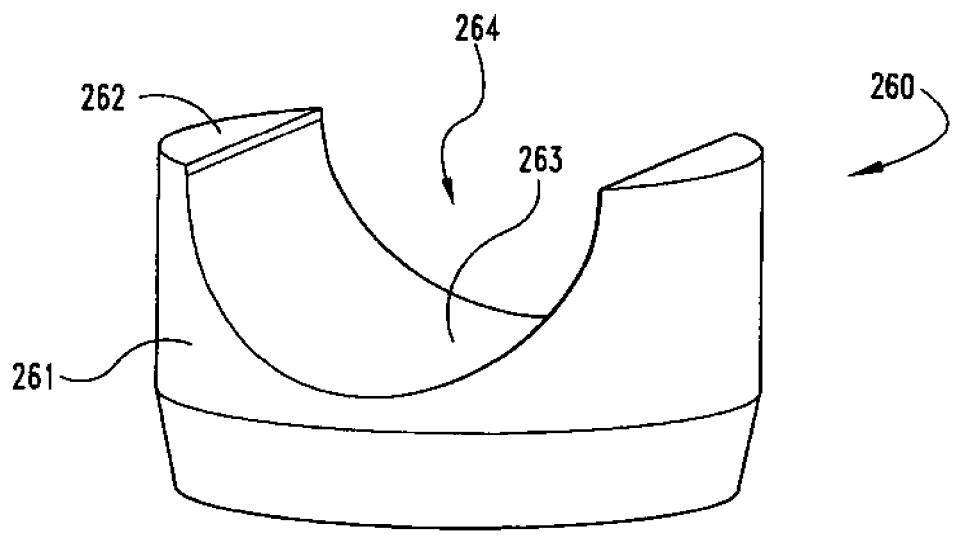
FIG. 20 is a prospective view of one embodiment of a friction insert for use in the present invention.

FIG. 20 is a perspective view of another embodiment of an insert 260 for use in the present invention. Insert 260 includes a substantially cylindrical body 261 having an upper surface 262 with a concave recess 264 formed therein. Insert 260 can be used in lieu of or in addition to insert 210. In a preferred embodiment, insert 260 is disposed in the aperture of the interconnection body or eyebolt such as those illustrated in FIGS. 1, 8, 10, and 12.

Figure 21:
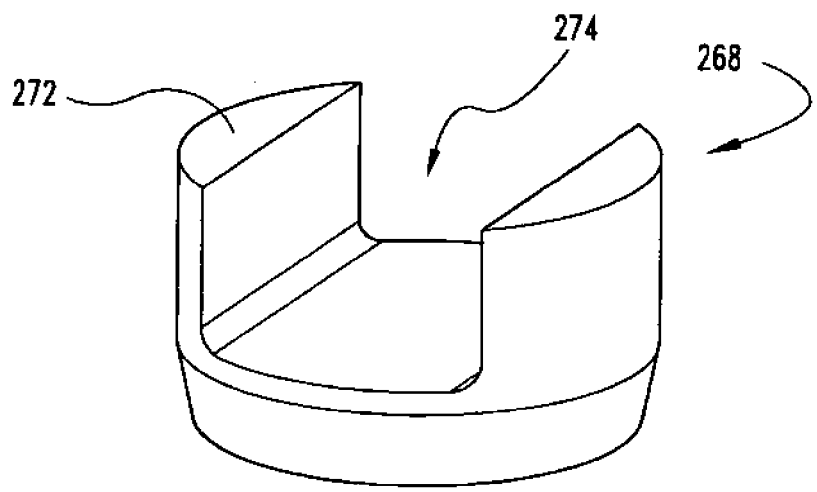
FIG. 21 is a prospective view of another embodiment of a friction insert for use in the present invention.

FIG. 21 is a perspective view of yet another embodiment of an insert 268 in accordance with the present invention. Insert 268 includes an upper surface 272 and a recess 274 formed therein. Recess 274 includes upwardly extending side walls and a bottom or trough 263 therebetween. Recess 274 is provided to exhibit a substantially rectangular or square cross-sectional area and is sized to receive a shaft having a rectangular cross-sectional profile. Insert 268 can be disposed in an eyebolt similar to insert 260 illustrated in FIG. 20 to receive and bear against a substantially square or rectangular shaft of a male connector member which has been inserted therein. The shaft of the connector member can rest against the bottom 263 of the recess 274. In one embodiment, the bottom 263 can be frictionally engaged with the shaft and thus secure the shaft within the interconnection body shaft.

In yet other embodiments, the present invention can include an insert formed as a circular O-ring provided to frictionally engage either a shaft of a connecting member and/or the stud of the interconnecting element.

Inserts 260 and 268 can be formed of a biocompatible material. Preferably inserts 260 and 268 are formed of a material that will induce restricted movement of the male shaft within the aperture. Examples of these materials include metallic materials, ceramics, composites, and preferably elastomeric materials.

Figure 22:
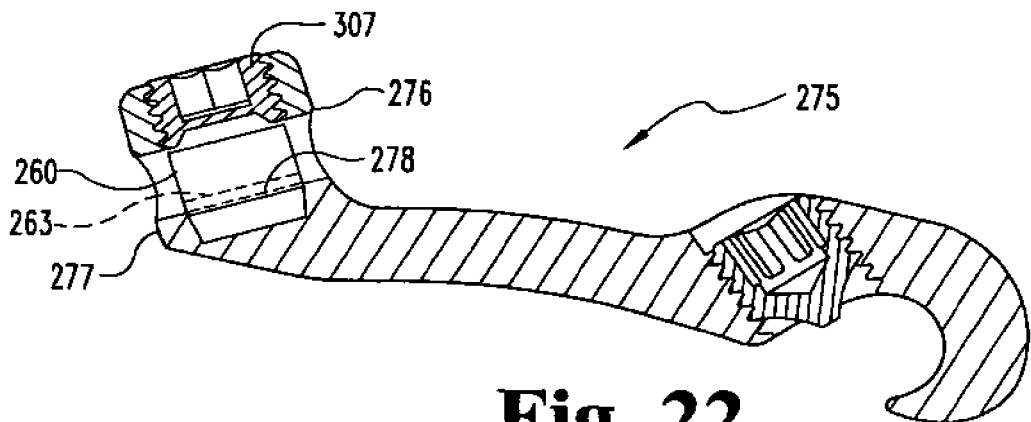
FIG. 22 is a cross-sectional view of a one-piece, female connector member and an interconnection element with a friction insert in accordance with the present invention.

Referring now to FIG. 22, a female interconnector member 275 is illustrated specifically for use with a frictional insert such as inserts 260 and 274. Interconnector member 275 includes an interconnecting body 276 carried on proximal end 277. An aperture 279 extends through interconnecting body 276. Aperture 279 is sized to receive a male connector member such as male member 12, 94, 176, 196, or 302. Additionally, interconnecting body 276 includes a well 278 within aperture 279. Insert 260 is disposed within well 278 with the concave recess 264 aligned an aperture 279. Insert 260 can receive or partly encircle the shaft of the male connector member received therein. Consequently, movement of the shaft within aperture 279 (and the concave recess 264) is restricted depending upon the amount force induced by tightening fastener 307. The components, i.e., the male and female connectors, insert, and fasteners, can be provided pre-assembled by the manufacturer to the surgeon. The pre-assembled components allow limited movement of the connectors and, consequently, facilitate the implantation of the interconnection assembly during surgery.

Figure 23:
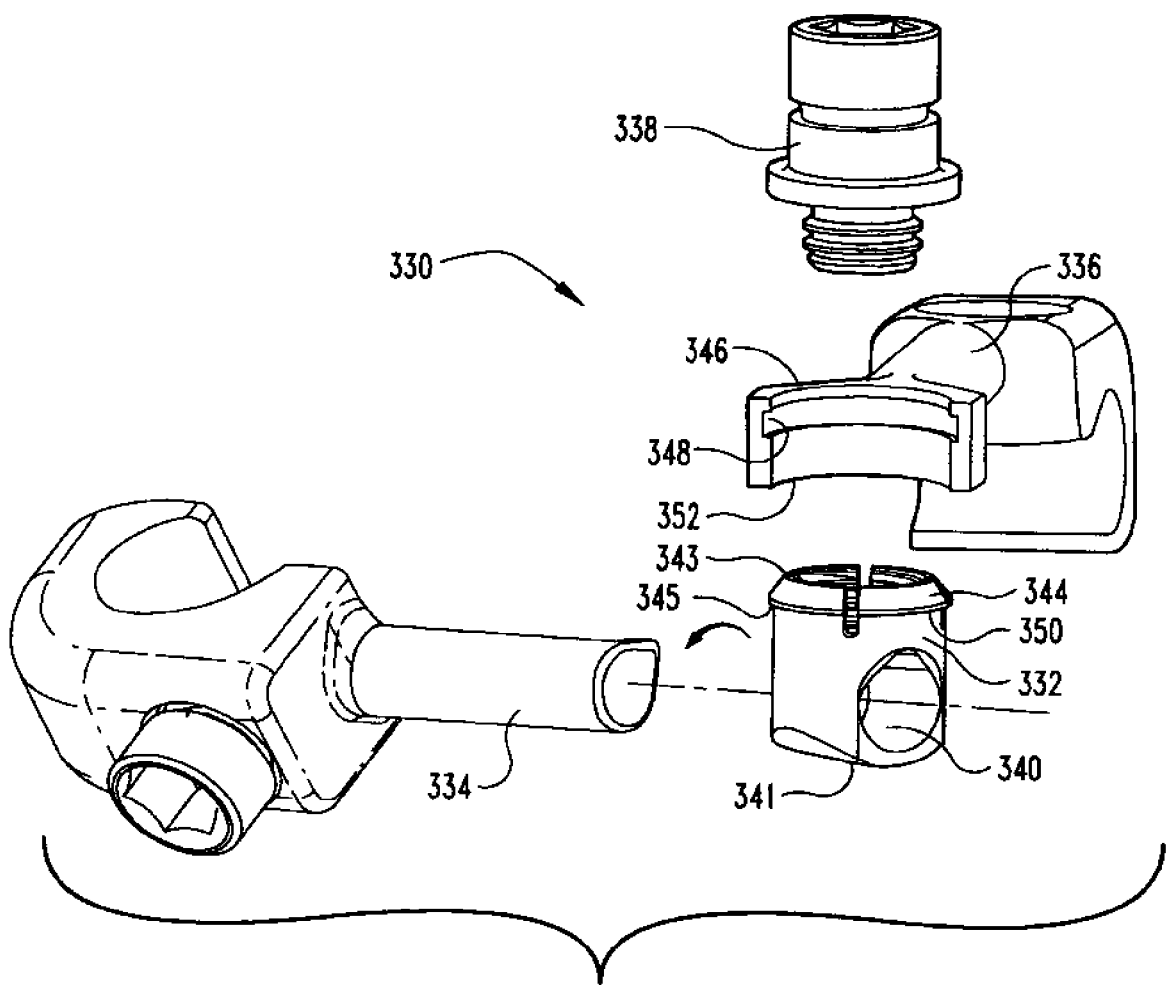
FIG. 23 is an exploded view of a connector assembly having a click-lock connection in accordance with the present invention.

FIG. 23 is an exploded partial view of yet another embodiment of an interconnecting assembly 330 in accordance with the present invention. Interconnecting assembly 330 includes an interconnecting element 332, a male connector member 334, a female connector member 336 (shown in cross-sectional view through body 346), and a fastener 338. Interconnecting element 332 is provided as a substantially cylindrical body having an aperture 340 extending therethrough. In a preferred embodiment, aperture 340 is provided as non-round, more preferably having an oval cross section. Aperture 340 is provided to slideably receive a portion of male connector member 334. Interconnecting element 332 includes a first end 342 and an opposite second end 341. First end 342 includes a rim or ridge portion 344 adapted to engage within the interior of a portion of female connector member 336. The combination of ridge portion 344 and female connector member 336 provides a click-lock engagement to initially secure the female connector member 336 to the interconnecting element 332 while still allowing relative movement of each component.

Figure 24:
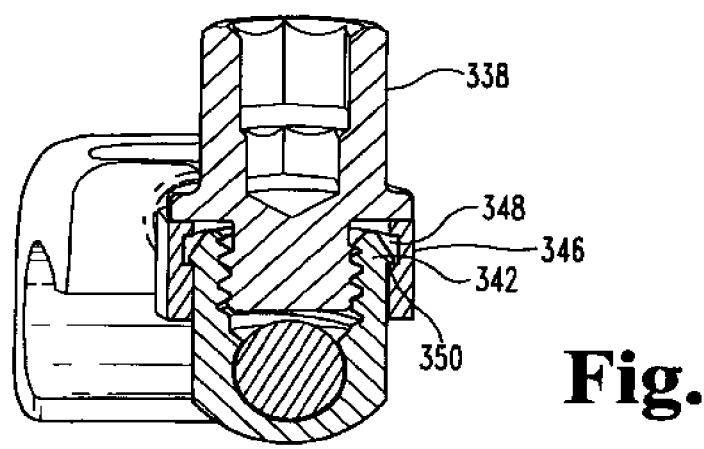
FIG. 24 is a cross-sectional view of a female connector member and the click-lock connection for use in the connector assembly of FIG. 23.
Figure 25:
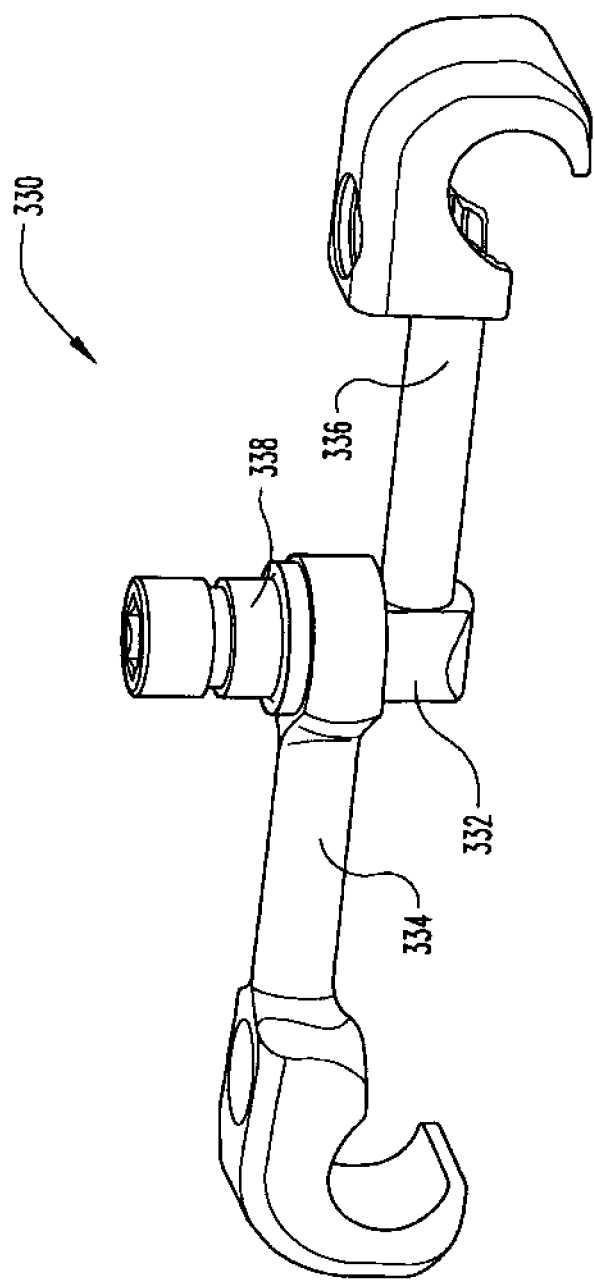
FIG. 25 is a perspective view of the connector assembly of FIGS. 23 and 24 pre-assembled in accordance with the present invention.
Figure 26:
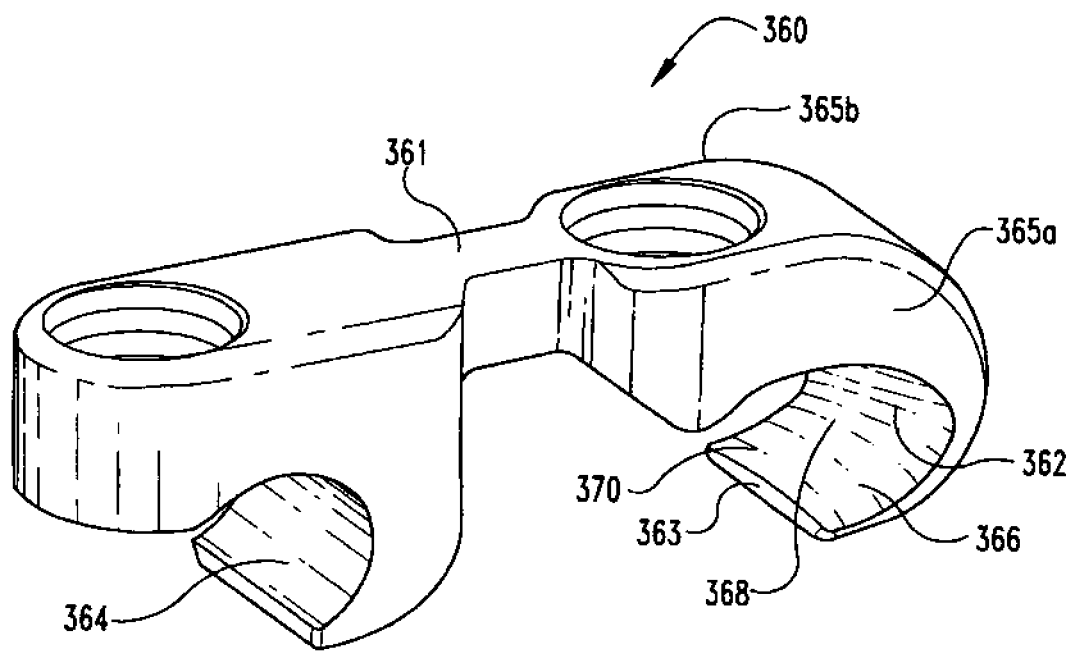
FIGS. 26 and 27 are perspective views of an alternative embodiment of a unitary connector in accordance with the present invention.
Figure 27:
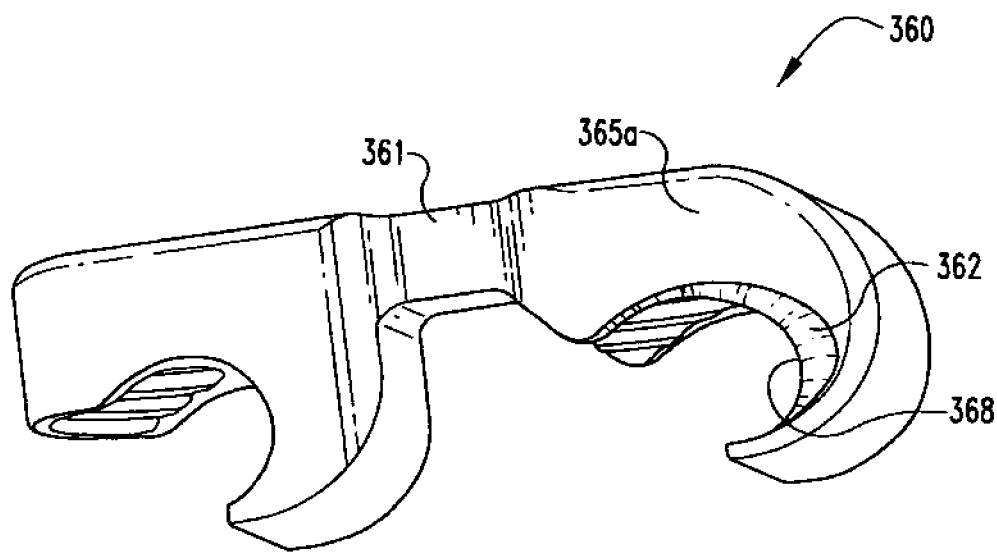
Figure 28:
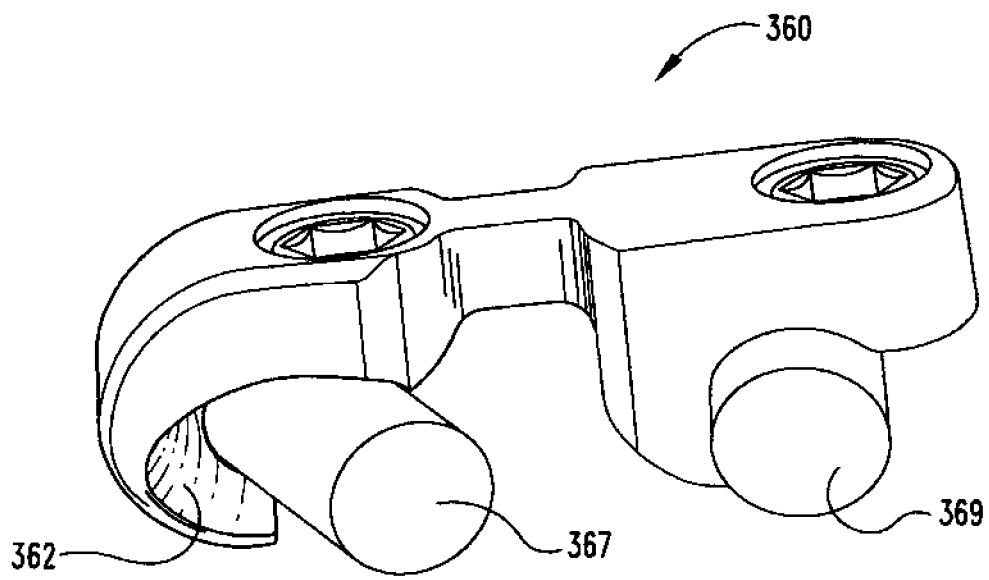
FIGS. 28 and 29 are perspective views of the unitary interconnector illustrated in FIGS. 26 and 27 secured to two spinal rods in accordance with the present invention.
Figure 29:
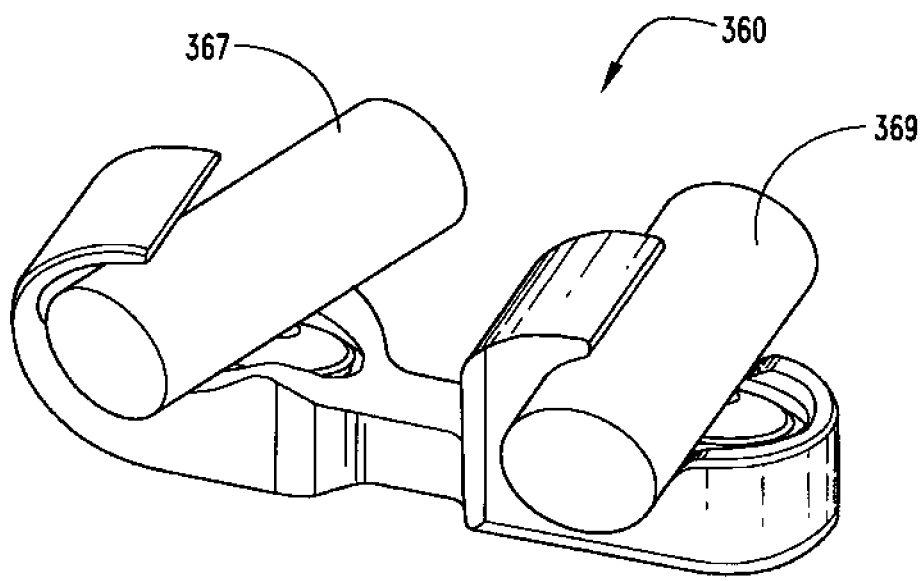

Referring additionally to FIG. 24, which illustrates a cross-sectional view of female connector member 336, it can be observed that the interior of the body 346 includes a groove 348 to engage and contact the ridge portion 344. When body 346 is initially inserted onto the top of interconnecting element 332, ridge portion 344 engages into groove 348. In preferred embodiments, ridge portion 344 is provided with a sloped or inclined surface extending from first end 343 to second end 345 to facilitate insertion into body 346. Additionally, ridge portion 344 includes a locking portion or step 350 that can bear against and contact the internal portion of groove 348 to prevent the female connector member 336 from backing out of the interconnecting element 332. This provides an initial locking connection between the two components. However, while thus engaged, each of male connector member 334, female connector member 336, and interconnecting element 332 are freely adjustable without requiring disengagement of any of these components.

Referring additionally to FIG. 24, a cross-sectional view of the interconnecting element 332 is illustrated. In preferred embodiments, the male connector member 334 and female connector member 336 can be locked in a desired orientation (relative to each other) by torqing down fastener 338 into the threaded interior of body 346. Tightening down fastener 338 serves to secure the female portion 336 to body 346. Additionally, the lower surface 352 of body 346 engages with a portion of shaft 354 as illustrated in FIG. 23.

FIGS. 25 through 29 illustrate another embodiment of an interconnecting assembly 360 in accordance with the present invention. Connecting assembly 360 can be provided as a dual connector. In preferred embodiments, the dual connector is provided as one-piece unit that includes two or more spinal rod connecting portions 364, 366 depending from a common rod or bar 361. In the illustrated embodiment, connecting portions 364 and 366 are aligned—substantially parallel with each other.

It can be observed that spinal rod connecting portion 366 is provided to include a saddle or ridge 368 extending along the circumferential interior of the hook portion 370. The interior surface 362 curves both vertically from bar 361 to tip 363 and laterally from a first side 365a to a second, opposite side 365b. In other embodiments interior surface 362 curves in a first direction and also curves in a second direction that is oblique to the first direction. In alternative embodiments, interior surface 362 curves in a second direction that is orthogonal to the first direction or at an angle that is either acute or obtuse to the first direction. Further, the amount of curvature or degree can vary as desired.

The saddle ridge 368 is provided to allow an included spinal rod to rest within the hook portion 370 at a variable angle with respect to a spinal rod that has been contained within portion 364. In alternative embodiments, both spinal rod securing portions 364 and 366 can include a ridge or saddle similar to 368 and surface 362. In this embodiment, the angles between the two included spinal rods 367 and 369 (illustrated in FIGS. 28 and 29) can vary widely. Furthermore, the two included spinal rods can be secured together while they lie in different planes, i.e., when the two rods do not lie in the same plane.

Figure 30:
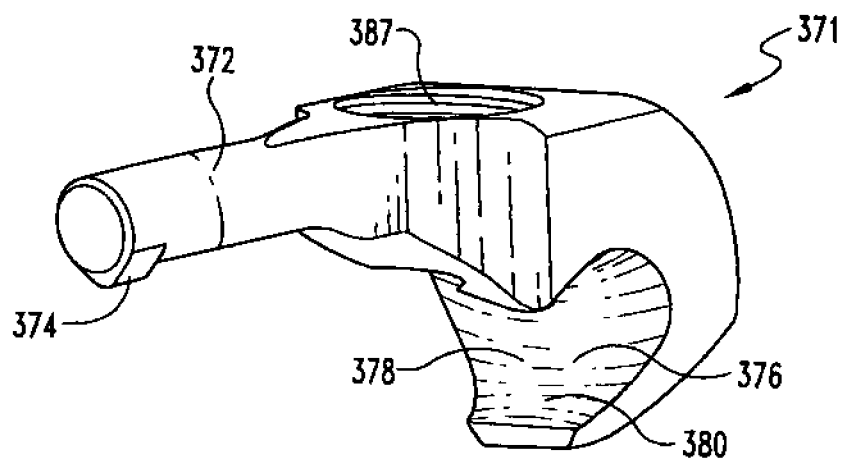
FIG. 30 is a perspective view of an alternative unitary interconnecting member for securing a spinal rod in accordance with the present invention.

FIG. 30 illustrates yet another embodiment of a male connector member 371. It can be observed that male connector member 371 includes a shaft 372 having a projection 374 for engaging with an interconnecting body similar to that shaft 26 and projection 28 of male connector member 12 in FIG. 1. Male connector member 371 includes a spinal rod securing portion 376 having a saddle or ridge 378 extended about the internal circumference of hook portion 380. Ridge 378 (similar to ridge 368) allows an included spinal rod to be secured in a variety of orientations. Additionally, as has been described with other male connector members in the present application, a threaded aperture 387 can be used in combination with a threaded fastener (see FIGS. 1, 6a and 6b) to bear against and secure an elongate member.

Figure 31:
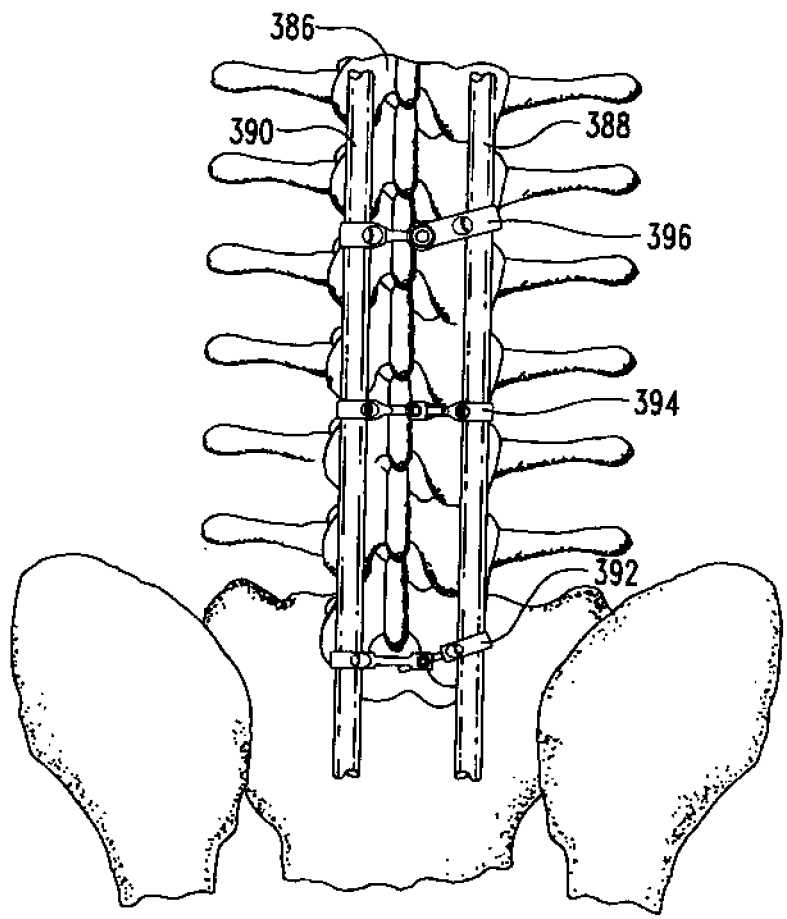
FIG. 31 is an illustration of a spinal column, two spinal rods secured to the spinal column, and a plurality of connector assemblies interconnecting the spinal rods in accordance with the present invention.

FIG. 31 is a diagrammatic illustration of a spinal column 386 including a pair of elongate members 388 and 390. Elongate members 388 and 390 can be spinal rods. Further, it will be understood that the elongate members can be either shorter or longer than illustrated. Additionally, the elongate members can be positioned to various locations on the spinal column and attached to different anatomical structures of the vertebrae. Elongate members 388 and 390 are interconnected with a plurality of interconnector assemblies 392, 394, and 396 provided as described herein. The interconnecting assemblies 392, 394, and 396 can be selected among any of those described in the present application including 10, 110, 174, 194, 246, 300, 310, 360, and 371. In some embodiments, the connector assemblies need not be the same connector assemblies; that is, connector assembly 392 need not be the same as 394, which need not be the same as 396. The various components of the spinal fixation systems described herein are preferably formed of a biocompatible material including stainless steel, titanium, and other suitable metals and/or metal alloys according to known methods.

Further, while various embodiments of a system for spinal fixation having specific components and structures are described and illustrated herein, it is to be understood that any selected embodiment can include one or more of the specific components and/or structures described for another embodiment where possible and as such are intended to be within the scope of the present invention.

Any reference to a specific directions, for example, references to up, upper, down, lower, vertical and horizontal and the like, is to be understood for illustrative purposes only or to better identify or distinguish various components from one another. These references are not to be construed as limiting in any manner to the system for spinal fixation and/or methods as described herein.

The present invention contemplates modifications as would occur to those skilled in the art. It is also contemplated that components and systems embodied in the present invention can be altered, rearranged, substituted, deleted, duplicated, combined, or added to other processes as would occur to those skilled in the art without departing from the spirit of the present invention. In addition, the various stages, steps, procedures, techniques, phases, and operations within these processes may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A cross-connector assembly for interconnecting a pair of orthopedic rods, said assembly comprising:
    an interconnection element including a first body having a first aperture formed therethrough and a stud extending from said first body in a direction orthogonal to said first aperture;
    a first rod connector including a first shaft terminating in a first rod engaging portion;
    a second rod connector including a second shaft terminating in a second rod engaging portion and having a second aperture formed therein with said stud of said interconnection element received within said second aperture; and
    a fastener configured to engage said stud to secure said first rod connector in position relative to said second rod connector; and wherein said interconnection element includes a pair of external flanges extending outwardly away from said stud, said second body of said second rod connector including a pair of internal flanges extending inwardly into said second aperture, wherein said external flanges of said interconnection element allow said internal flanges of said second body to pass through gaps between said external flanges during assembly, and wherein upon rotation of said second body said external flanges of said interconnection element engage said internal flanges of said second body to retain said second rod connector in engagement with said interconnection element.

2. The assembly of claim 1 wherein in a first orientation between said first rod connector and said interconnection element an end portion of said first shaft is slideably positionable through said first aperture and upon rotation of said first rod connector relative to said interconnection element from said first orientation to any other orientation said end portion is prevented from sliding back through said first aperture to thereby secure said first rod connector to said interconnection elements.

3. The assembly of claim 2 wherein said first shaft of said first rod connector is axially slidable within said first aperture of said interconnection element when said first rod connector is in said any other orientation until said assembly is secured with said fastener.

4. The assembly of claim 2 wherein said first aperture in said first body of said interconnection element includes a lobed shape portion; and wherein said first rod connector includes a lobe extending laterally from said end portion of said first shaft and projecting toward said first rod engaging portion; and wherein in said first orientation between said first rod connector and said interconnection element said lobe of said first shaft is slideably positionable through said first aperture and upon rotation of said first rod connector relative to said interconnection element from said first orientation to said any other orientation said lobe prevents said end portion from sliding through said first aperture to thereby secure said first rod connector to said interconnection element.

5. The assembly of claim 1 wherein said first aperture extends from an upper portion positioned adjacent said stud to an oppositely positioned lower portion, said lower portion defining a semi-circular configuration and said upper portion defining a non-circular configuration.

6. A cross-connector assembly for interconnecting a pair of orthopedic rods, said assembly comprising:
    a first rod connector including a first shaft terminating in a first body having a channel therethrough;
    a second rod connector including a second shaft defining a longitudinal axis and terminating on a first end with a rod engaging portion and on an opposite second end with a second body, said second body having a first aperture therein defining a first central axis, said first end of said second rod connector also including a second aperture therein defining a second central axis positioned to lie at an angle relative to the first central axis;

an interconnection element having a third body that includes a third aperture therein for receiving a portion of said first shaft and a stud protruding upwardly from said third body;

an insert positioned over said stud and having a lower surface defining a concave portion configured to engage said first shaft of said first rod connector on opposite sides of said stud, said insert having an upper portion positioned in said first aperture of said second body; and a fastener extending through said first aperture of said second body and into an internal recess of said insert to fixedly engage said stud to thereby secure said orientation of said first rod connector relative to said second rod connector.

7. The assembly of claim 6 wherein said insert includes a slit along a vertical axis, said slit extending between and opening at opposite ends of said insert.

8. The assembly of claim 7 wherein said slit intersects said concave portion of said lower surface.

9. The assembly of claim 6 wherein said fastener engages said insert to thereby secure said first rod connector in a select orientation relative to said second rod connector.

10. The assembly of claim 6 wherein said fastener engages said second body of said second rod connector to thereby secure said first rod connector in a desired orientation relative to said second rod connector.

* * * * *